United States Patent [19]

Tell

[11] Patent Number: 4,554,761

[45] Date of Patent: Nov. 26, 1985

[54] POLLINATING BAG

[75] Inventor: Joseph M. Tell, West Des Moines, Iowa

[73] Assignee: Carpenter Paper Company, Des Moines, Iowa

[21] Appl. No.: 616,246

[22] Filed: Jun. 1, 1984

[51] Int. Cl.[4] .............................................. A01G 7/00

[52] U.S. Cl. .......................................... 47/1.41; 47/26

[58] Field of Search .................. 47/1.41, 26; 383/124, 383/123, 125; 428/138

[56] References Cited

U.S. PATENT DOCUMENTS

| | | | |
|---|---|---|---|
| 904,168 | 11/1908 | Widmer | 383/124 |
| 3,227,359 | 1/1966 | Hanlon | 383/124 |
| 3,387,640 | 6/1968 | Butler | 383/106 |
| 4,159,596 | 7/1979 | Downing | 47/26 |
| 4,291,082 | 9/1981 | Stall | 383/102 |

*Primary Examiner*—Robert A. Hafer
*Assistant Examiner*—Bradley M. Lewis
*Attorney, Agent, or Firm*—Henderson & Sturm

[57] ABSTRACT

A cover for selectively protecting a plant reproductive organ from pollination. Design features of the invention make it particularly useful in the hybridization of corn plants. The cover slips over the shoot of the corn plant when it is in the early stages of development and is left in place until the shoot is ready for pollination. The manner of construction imparts a bias to the cover towards drawing inward, assuring that it will remain in place during high winds, and allowing for expansion as the shoot increases in size. The cover is transparent to enable workers to observe developmental stages. The cover material is vapor permeable to prevent unwanted condensation from destroying transparency and to discourage the growth of mildew, fungus and bacteria.

6 Claims, 7 Drawing Figures

10
19
23
10
19
12
22

19
10
23
15
12
22

10
19
17
17
11
12

7.
19
10
6.
7.
6.
13
17
17
12

19
10
15
16
18
11
17
12

18
17
13
14
17
10
18
16
11
16

19

POLLINATING BAG

TECHNICAL FIELD

The present invention relates generally to equipment used in plant hybridization, and more particularly to the hybridization of corn plants.

BACKGROUND ART

Part of the hybridization process involves the protection of the reproductive organs of a parent plant from unwanted airborne pollen by covering it at an early stage. After the plant has reached a sufficient level of development, a worker removes the cover and pollinates the plant with pollen from another carefully selected plant. A standard cover in the industry is constructed by folding and gluing a sheet of white paper to form a thin flat tube, then folding one end over so that the tube is closed. The standard design is not biased toward drawing inward, so it is vulnerable to high winds which tend to blow it off the corn shoot. Care must be taken in placing and checking the standard cover since it does not expand easily to allow for the growth of the shoot. It is not uncommon for the standard cover to burst if the shoot becomes too large, rendering the plant useless for the purpose of hybridization. To remedy this, workers are instructed to watch for covers ready to burst and to loosen them by sliding them upward one-half to one inch if necessary. This procedure is time consuming and requires careful observation.

When using the standard paper cover, it is difficult to determine if the plant is ready for hybridization since the standard cover device does not permit observation of the shoot within. Therefore, it may be necessary to sacrifice one or more plants by removing their covers to observe the stage of development. Once the cover is removed, airborne pollen from unwanted sources may enter and the plant is rendered unusable.

A transparent cover from Poland has been used, at least experimentally. It is analogous in design to the aforementioned standard in the industry, since it is thin and flattened but additionally it is formed by sewing two rectangular pieces of plastic together at three edges. Thus, in its construction, it has most of the shortcomings of the standard of the industry. The plastic from which it is constructed is brittle, traps moisture, fogs easily, and promotes the growth of bacteria and fungi.

Consequently, there is a need for a cover which will remain in place, expand automatically without bursting, allow for easy observation of the development of the plant, and will not provide an environment which encourages the growth of undesirable bacteria and fungi.

DISCLOSURE OF THE INVENTION

The present invention relates to a cover for selectively preventing a plant reproductive organ from pollination. The cover includes a front and rear wall, a pair of folded and creased side walls sealingly attached to said front and rear walls, with the front, rear and side walls meeting together at the top, then being folded over and sealed to preserve an inward crease of the end walls so as to bias the walls toward drawing inwardly together, yet allowing for needed expansion.

An object of this invention is to provide a cover for a shoot in a hybridization process which will remain tightly in place during high winds, yet is automatically expandable as the plant shoot grows.

Another object is to obviate the need for the close observation and adjustment required in the past to prevent bursting of a cover of the aforementioned type.

A further object of the present invention is to provide a cover which allows for a clear view of the state of development of a shoot within the cover.

Still another object is to find a material for shoot covers which will remain stable, clear and dry even in conditions encouraging condensation of moisture, which could obscure the view and promote the growth of bacteria, mold, mildew and fungi.

Other objects, advantages and novel features of the present invention will become apparent from the following detailed description of the invention when considered in conjunction with the accompanying drawings.

BEST MODE FOR CARRYING OUT THE INVENTION

Figures 1, 2, 3, 4, 5, 6, 7:
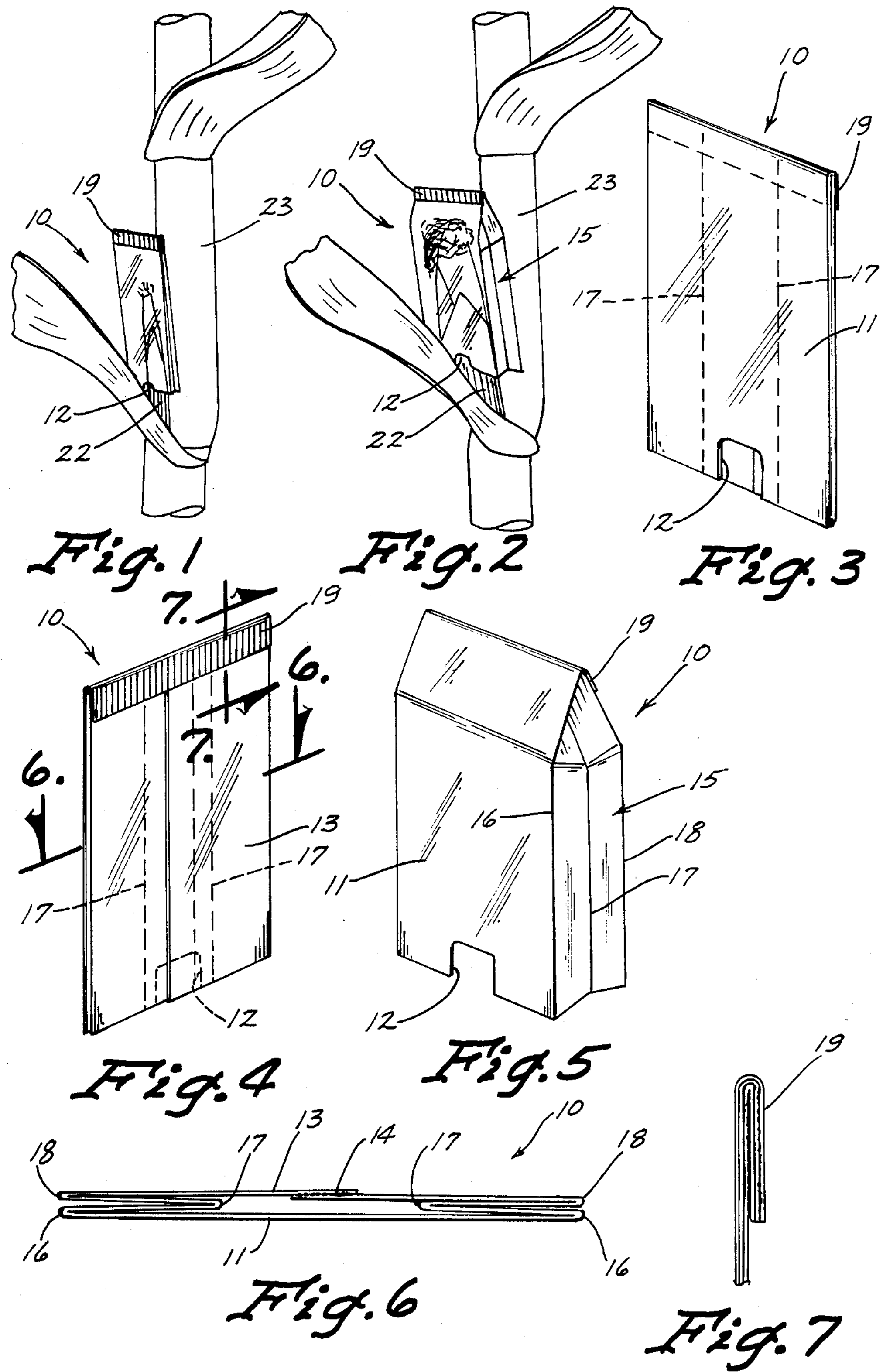
FIG. 1 is a perspective view of a cover constructed in accordance with the present invention as it would look when initially placed on an undeveloped reproductive organ (shoot) of a corn plant.
FIG. 2 is a perspective view of the cover of FIG. 1 after the shoot has grown in size and matured, showing the expanded walls of the cover.
FIG. 3 is a perspective view of the front and unexpanded walls as the cover appears before or after use thereof.
FIG. 4 is a perspective view of the back, an unexpanded side wall, and the sealed fold which forms the closed top of the cover as it appears before or after use.
FIG. 5 is a perspective view of the cover along, shown in an expanded position.
FIG. 6 is a cross-sectional view of the cover taken along line 6—6 of FIG. 4.
FIG. 7 is a partial enlarged cross-sectional view of the cover taken along line 7—7 of FIG. 4 and showing a heat sealed and glued fold which forms the closed top of the cover.

Referring now to the drawings wherein like reference numerals designate identical or corresponding parts throughout the several views, FIGS. 3–7 show the cover (10) constructed in accordance with the present invention. The cover (10) is constructed of a transparent plastic material, specifically an uncoated, heat sealing, vapor permeable polypropylene film. A front (11), FIG. 3, has an optional thumb notch (12) for facilitating ease of opening of cover (10). A back (13), FIG. 4, has a sealed seam (14). The two sides (15) are folded inwardly to permit controlled expansion, as best shown in FIG. 6. FIGS. 2 and 5 show the positions of the folded sides (15) when the cover (10) is expanded. By heating the cover (10) during the folding process, the creases (16), (17) and (18) are permanently formed into the cover (10). A first side panel (20) is formed between creases (16) and (17), and a second side panel (21) is formed between creases (17) and (18). The opposite side is identical to the side shown in FIG. 5.

A top (19) is formed, as best shown in FIG. 7, by folding over the unexpanded cover and sealing the folded top portion (19) with heat and glue. Note that the folding of the seams (16), (17) and (18) is preserved during such folding and sealing process. This biases the walls (11) and (13) towards each other which allows for needed expansion as the shoot grows and develops. (See FIGS. 1 and 2). Also, since the cover device (10) is resilient, and because of the particular folded construction, it will always tend to return to its original FIGS. 3 and 4 position. This will cause the cover device (10) to cling tightly to a shoot (22) as shown for example on corn stalk (23) in FIGS. 1 and 2, whether the shoot (22) is in a small developing stage as shown in FIG. 1, or in an enlarged, more developed stage as shown in FIG. 2. This inherent biasing of crease (17) and walls (11) and (13) toward the shoot (22) prevents the cover (10) from blowing off of the shoot (22) during high winds or other outside forces, and yet allows the shoot (22) to expand without bursting.

The preferred approximate dimensions of the cover parts are as follows: Sides are 7"×4". Infolded ends are triangularly-shaped with a base of 2½ inches, a height of 7 inches, and folded creases (16), (17) and (18) on each side which perpendicularly bisects the base and bisects the apex of the triangle. The top fold, FIG. 7, is ½ inch wide. The seam (14) on the back overlaps by ¾ of an inch.

The invention is utilized as shown in FIGS. 1 and 2. Firstly, the cover is slightly expanded and slipped over the immature shoot of the plant. This prevents pollen from overhead corn tassels from reaching the shoot until the workers are ready to pollinate the plant from a specially selected source. The biasing of the cover (10) holds it securely in place. FIG. 2 shows the matured shoot (20), which has grown in size from the FIG. 1 size. The folded sides (15) of the cover have expanded to allow for growth, yet the inherent biasing forces continue to hold the cover (10) in place despite changes in the size of the shoot (22). A worker can observe the condition of the corn silk through the cover (10) to determine when the plant is ready for pollination. The cover is removed for the pollination process.

Considerable inventive effort went into selecting the material used in making the cover, since not all clear plastic materials are suitable. The cover material must be readily permeable by water vapor. If not, condensation on the inside of the cover will prevent observation by causing a moist environment within the cover which encourages the growth of bacteria, mold, mildew and fungus. Also, some plastics are adversely affected by sunlight. They yellow, become brittle and lose their plasticisers at a rapid rate. The above identified problems have been solved by utilizing an uncoated, heat sealing, vented polypropylene film of approximately 0.00122 inch in thickness. The material is relatively stiff, but not brittle, does not fog easily, has good water vapor and oxygen transmission rates, and has resilient properties.

Many modifications and variations of the present invention are possible in light of the above teachings. It is therefore to be understood that, within the scope of the appended claims, the invention may be practiced otherwise than as specifically described.

I claim:

1. A plant reproductive organ antipollination barrier cover comprising:
cover means constructed of a transparent, uncoated, heat sealing, vented polypropylene film for extending over and around a plant reproductive organ for selectively preventing said reproductive organ from pollination, said cover means including:
a front panel;
a rear panel;
first side closure means for sealingly connecting said front and rear panels along one side thereof, said side means including a first and second side panel;
first crease means for biasing said first side panel and said rear wall towards each other;
second crease means for biasing said first and second side panels towards each other;
third crease means for biasing said second side panel and said front panel toward each other;
second side closure means for sealing connecting said front and rear panels along the other side thereof; and
end closure means for sealing one end of said front and rear side panels and said first and second side means with respect to each other whereby said one end will be sealed to prevent the entry of pollen into said one end of said closure means, and wherein said front wall, rear wall, first side panel and second side panel are all secured together along a substantially straight seam oriented transversely with respect to said first, second and third crease means and wherein said first, second and third crease means extend to said seam.

2. The cover of claim 1 wherein said second side closure means includes a third and fourth side panel;
fourth crease means for biasing said third side panel and said rear wall towards each other;
fifth crease means for biasing said third and fourth side panels towards each other; and
sixth crease means for biasing said fourth side panel and said front panel towards each other.

3. The cover of claim 1 wherein said plastic material is a vapor permeable compound to prevent condensation of moisture from obscuring the view of the plant reproductive organ covered by the device, and to discourage the growth of mildew, fungus and bacteria.

4. The cover of claim 1 wherein one of said front and rear panels has a notch means disposed therein for permitting easy opening of said cover means.

5. The cover of claim 1 wherein said seam was formed by heating the front, rear, first and second side panels while pressing them together.

6. The cover of claim 5 wherein said one end of said front, rear and side panels are folded over and glued to one of the front and rear panels.

* * * * *